United States Patent [19]

Borsanyi et al.

[11] Patent Number: 4,898,583
[45] Date of Patent: Feb. 6, 1990

[54] IMPLANTABLE PATIENT-ACTIVATED FLUID DELIVERY DEVICE AND OUTLET VALVE THEREFOR

[75] Inventors: Alexander S. Borsanyi, Newport Beach; Russell J. Redmond, Goleta, both of Calif.

[73] Assignee: Baxter Healthcare Corporation, Deerfield, Ill.

[21] Appl. No.: 195,770

[22] Filed: May 18, 1988

[51] Int. Cl.$^4$ .............................................. A61N 1/00
[52] U.S. Cl. ........................................................ 604/153
[58] Field of Search ..................................... 604/8–10, 604/31, 33, 93, 116, 131, 151, 153, 175, 181–183, 185, 186, 244, 246, 247, 249, 891.1; 137/75, 843, 852

[56] References Cited

U.S. PATENT DOCUMENTS

| | | | |
|---|---|---|---|
| 2,638,127 | 5/1953 | Griswold | 137/859 |
| 3,768,508 | 10/1973 | Schulte | 604/9 |
| 3,769,982 | 11/1973 | Schulte | 28/350 |
| 3,827,439 | 8/1974 | Schulte | 128/350 V |
| 3,850,190 | 11/1974 | Carlson | 137/859 |
| 4,013,074 | 3/1977 | Siposs | 128/260 |
| 4,190,040 | 2/1980 | Schulte | 128/1 R |
| 4,193,397 | 3/1980 | Tucker | 128/207.19 |
| 4,258,711 | 3/1981 | Tucker | 128/207.19 |
| 4,265,241 | 5/1981 | Portner | 128/260 |
| 4,360,019 | 11/1982 | Portner | 128/213 R |
| 4,400,169 | 8/1983 | Stephen | 604/49 |
| 4,437,457 | 3/1984 | Trick | 128/1 R |
| 4,487,603 | 12/1984 | Harris | 604/152 |
| 4,496,343 | 1/1985 | Prosl | 604/86 |
| 4,511,355 | 4/1985 | Franetzki | 604/131 |
| 4,543,088 | 9/1985 | Bootman | 604/93 |
| 4,544,371 | 10/1985 | Dormandy | 604/891 |
| 4,548,607 | 10/1985 | Harris | 604/891 |
| 4,557,722 | 12/1985 | Harris | 604/9 |
| 4,560,375 | 12/1985 | Schulte | 604/9 |
| 4,572,168 | 2/1986 | Fischell | 128/79 |
| 4,588,394 | 5/1986 | Schulte | 604/9 |
| 4,594,058 | 6/1986 | Fischell | 417/413 |
| 4,604,090 | 8/1986 | Reinicke | 604/118 |
| 4,626,244 | 12/1986 | Reinicke | 604/141 |
| 4,627,832 | 12/1986 | Hooven | 604/9 |
| 4,634,427 | 1/1987 | Hannula et al. | 604/185 |
| 4,639,244 | 1/1987 | Rizk | 604/19 |
| 4,668,231 | 5/1987 | de Vries et al. | 604/891.1 |

OTHER PUBLICATIONS

United States Statutory Invention Registration H150.

*Primary Examiner*—C. Fred Rosenbaum
*Attorney, Agent, or Firm*—Tilton, Fallon, Lungmus

[57] ABSTRACT

An implantable fluid delivery device having a deformable casing containing a fluid reservoir, a compressible pump housing, and inlet and outlet valves for controlling the flow of metered amounts of fluid from the reservoir to a catheter when a target zone of the casing's top wall is depressed. The construction and operation of the outlet valve result in the generation of a tactile feedback signal transmitted through the target zone to inform a user that a measured amount of fluid has been discharged from the device.

5 Claims, 3 Drawing Sheets

IMPLANTABLE PATIENT-ACTIVATED FLUID DELIVERY DEVICE AND OUTLET VALVE THEREFOR

BACKGROUND OF THE INVENTION

Various implantable devices have been disclosed in the prior art that may be activated by ambulatory patients when the administration of measured doses of therapeutic agents is required. For example, cancer patients suffering from terminal lower torso cancer may require routine injections of morphine, either epidurally or intrathecally, and, upon receiving such injections, are sufficiently relieved of the symptoms of pain to move about and perform many routine and normal functions. Other chronic ailments also require frequent dosages of therapeutic agents in the treatment of chronic conditions, such as insulin in the case of diabetes. Implantable devices capable of delivering measured amounts of medicament on demand are disclosed in U.S. Pat. Nos. 4,634,427, 4,548,607, 4,588,394, 4,557,722, 4,544,371, and 4,543,088. Other United States patents of general interest pertaining to implantable pumping or infusing systems are U.S. Pat. Nos. 4,560,375, 4,258,711, 3,769,982, 3,827,439, 4,013,074, 4,265,241, 4,360,019, 4,487,603, 4,496,343, 4,511,355, 4,604,090, and 4,627,832. Reference may also be had to United States Statutory Invention Registration H150.

SUMMARY OF THE INVENTION

Despite the attention that has been directed in recent years to the development of implantable drug delivery systems, prior devices have often been deficient in significant respects. The recognition of such deficiencies is considered to be one of the important aspects of this invention, along with the discovery and development of the means for overcoming those shortcomings. Unlike many of the prior devices, the fluid delivery device of this invention is formed of soft and deformable (preferably elastomeric) material capable of being worn comfortably and effectively in implanted condition over an extended period. In spite of its compliant outer casing, the device has a relatively rigid internal structure that serves to support various operative elements, such support also performing the functions of distributing pumping forces produced by finger pressure and protecting the casing (as well as interior elements) against damage and possible leakage during refilling operations.

The compactness of the device and its ease of operation result partly from the fact that its top wall has a central target zone that may be easily located by touch (even when the device is implanted) and that serves as both the pump-actuating site against which finger pressure is exerted when drug delivery is needed ad as the site for medicament injection when refilling of the reservoir is required. Enhanced self-sealing properties of the top wall and its underlying structure, coupled with a relatively rigid protective shield interposed between the top wall and the pump assembly, helps insure that the device may be easily refilled without risk of internal damage or leakage.

Even though the soft, resilient casing of the device yields or deforms with body movements and in response to both internally and externally applied forces, fluid pressure equalization within the device insures that pump activation and drug delivery do not occur unless directed and localized force is applied specifically to the target zone—a force that can be expected to be applied only intentionally.

Furthermore, the valve mechanism of the system resists activation until the locally-applied force reaches a predetermined magnitude. Unless a selected force within a range of, say, 10 to 20 pounds per square inch is applied to the central target zone of the device's top wall, the outlet valve will remain in closed condition. Of further significance is the fact that when sufficient localized force is so applied, the outlet valve will break open with sufficient suddenness and completeness to provide tactile feedback to the user. Through a sense of touch, a user may therefore determine that the device has indeed been activated and a metered amount of medicament has been discharged.

In brief, the implantable fluid delivery device includes a casing formed of soft, deformable polymeric material, preferably elastomeric material, having top and bottom walls defining a fluid reservoir therebetween. A rigid support plate is disposed within the casing and divides the reservoir into upper and lower chambers that communicate with each other through an opening in the plate. Compressible pumping means is mounted upon the plate within the upper chamber and includes a deformable pump housing that defines a pump cavity with a first passage connecting that cavity with the lower chamber of the reservoir. A second passage connects the same cavity with the outlet port of the device, and check valves are positioned to control flow through the respective passages.

The top wall of the casing includes a flexible pump-actuating zone. Connecting means in the form of a self-sealing septum combined with a rigid cover plate operatively connect the top wall's pump actuating zone with the pump housing. The self-sealing properties of the piercable septum are enhanced by a construction that maintains that septum in a partially-compressed state. Although the casing and many of the components contained within it are readily deformable, being formed of silicone rubber or other suitable material and although build up of fluid pressure due to unexpected compressive loads on the device is possible, pressure equalization within the reservoir, on opposite sides of elements such as the deformable pump housing and the check valve for the second passage, insure that deformation of the casing will not result in fluid delivery unless such deformation specifically includes depression of the target zone of the top wall in the direction of the compressible pump.

A porous metal filter is mounted upon the support plate at the entry to the first passage leading from the reservoir to the pump cavity. In addition to filtering fluid, the filter also performs a rate controlling function and therefore prevents surges of fluid, produced by compressive deformation of the device's deformable casing, that might otherwise cause damage to the pump assembly. Channel-defining ribs within the reservoir also function to equalize pressure within that reservoir and prevent obstructive contact with the rigid filter that might block fluid flow to the pump cavity.

The outlet valve, which functions as a check valve in the second (outlet) passage, is cup-shaped with a lower surface that cooperates with the flexible annular lip of the valve seat to maintain the valve in sealed condition throughout early stages in the deformation of the valve member as it moves towards an open condition. A sharp breakaway occurs when the flexible lip reaches its limit of deformation and the valve member proceeds to its fully open position, at which time the breakaway action and sudden release of pressure offer tactile feedback to the patient, signalling that a measured volume of medicament has been (or is being) discharged by the device.

Other features, objects, and advantages will become apparent from the specification and drawings.

DRAWINGS

DETAILED DESCRIPTION OF PREFERRED EMBODIMENT

Figure 2:
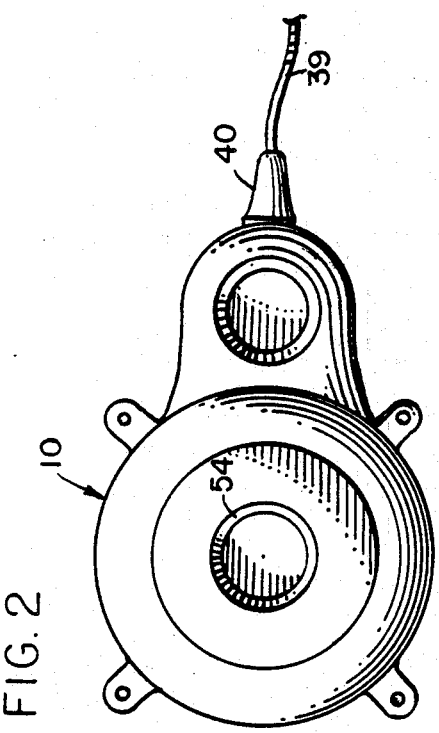
FIG. 2 is a top plan view.
Figure 1:
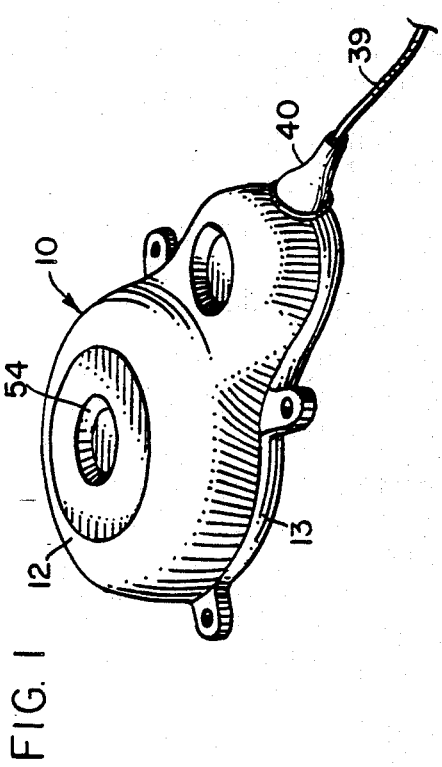
FIG. 1 is a perspective view of an implantable fluid delivery device embodying this invention.
Figure 3:
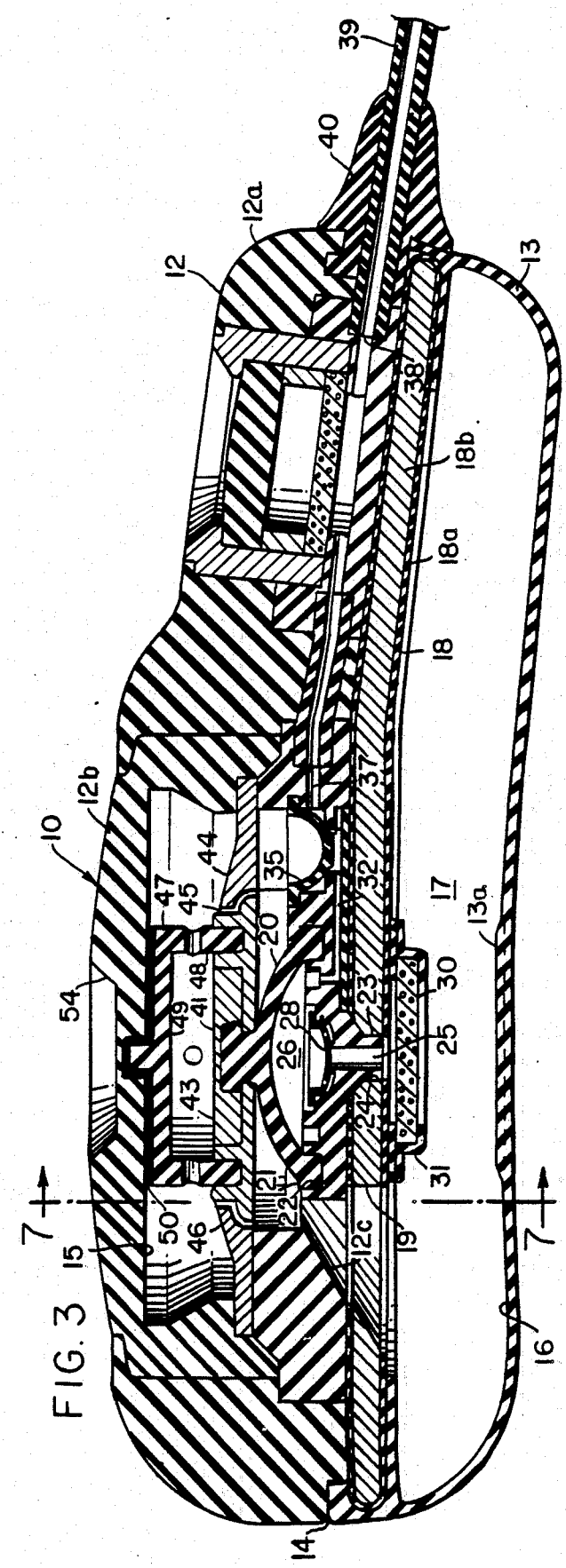
FIG. 3 is an enlarged longitudinal vertical sectional view of the device.

Referring to the drawings, and particularly to FIGS. 1–3, the numeral 10 generally designates an implantable delivery device having a casing 11 formed of soft, deformable polymeric material. While various materials having such properties might be used, an elastomeric material such as silicone rubber has been found particularly effective because of its deformability, recoverability, durability, and biocompatability. Viewed generally, the casing includes preformed (molded) upper and lower walls 12 and 13 that are sealed together along a horizontal midline 14. To facilitate manufacture, the upper wall 12 may be formed in two or more sections that allow the prefabrication of subassemblies. Thus, in the illustration given, upper wall 12 includes main section 12a, central section 12b, and inner section 12c. The central and inner sections together define an upper chamber 15, whereas the bottom wall defines a lower chamber 16. The two chambers communicate and together define an enlarged reservoir 17.

Figure 7:
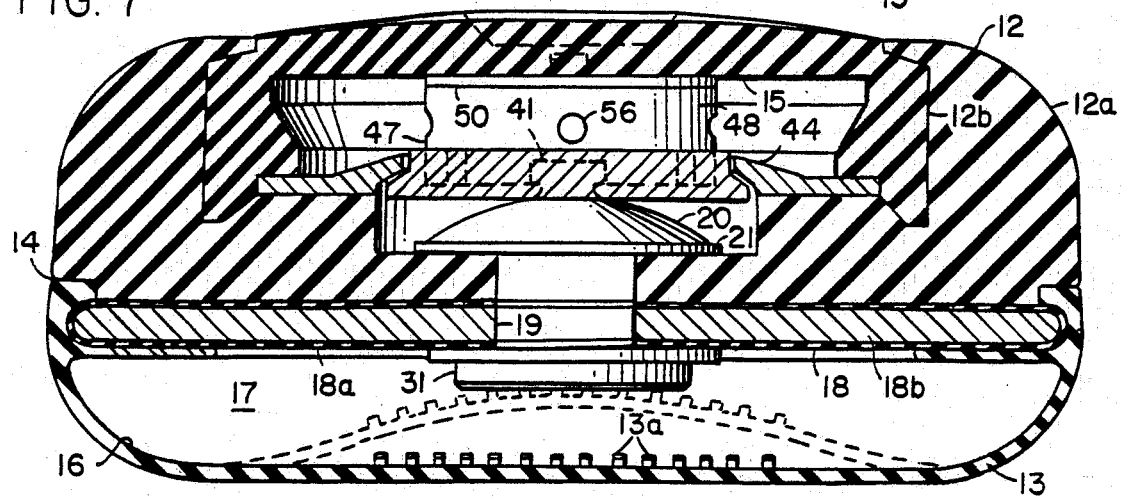
FIG. 7 is a transverse sectional view taken along line 7—7 of FIG. 3.

A relatively rigid support plate 18 is interposed between the upper and lower chambers of the reservoir 17 and, as shown most clearly in FIGS. 3 and 7, extends substantially the full width and length of the casing. The plate is sandwiched between the upper and lower walls 12 and 13 and, if desired, may be provided with an outer layer 18a of silicone rubber or other suitable material to enhance biocompatability and facilitate adhesive attachment of the parts. The core 18b of the support plate may be formed of any tough and rigid material, including metallic and ceramic materials, although a polymeric material such as polycarbonate is believed particularly suitable. Opening 19 through the support plate 18 places the upper and lower chambers 15, 16 of the reservoir in communication with each other. In use of the device, at least the lower chamber of the reservoir would contain a liquid medicament to be discharged in metered amounts upon actuation of the device; however, for clarity of illustration such fluid is not depicted in the drawings.

The pumping means for the device is located in the upper chamber 15 of the reservoir and is supported upon plate 18. The pumping means includes a dome-shaped pump housing 20 formed of silicone rubber or other suitable elastomeric material. The rim 21 of the pump housing is secured within an annular channel 22 provided in the upper surface of inner wall section 12c, and a downwardly-projecting stem portion 23 of that wall section projects through an opening 24 in the rigid support plate. Inlet flow passage 25 extends through the stem portion 23 and places the pump chamber or cavity 26 in communication with the lower chamber 16 of the reservoir. An annular valve seat 27 is provided at the upper end of passage 25 and is normally engaged by a dish-shaped elastomeric membrane valve member 28 that has its circular outer peripheral portion secured to wall section 12c. Like other components of the drug delivery device, the membrane valve member 27 may be formed of silicone rubber. As shown most clearly in FIGS. 4–6, the valve member is provided with openings 29 therethrough that are located outboard of valve seat 27 and that therefore allow flow of fluid between passage 25 and pump chamber 26 only when the valve member 28 is urged away from valve seat 27.

Directly below the pump, and mounted along the underside of the support plate 18, is a rigid filter member or disc 30. The disc may be formed of sintered metal or a fine metallic mesh and is secured in place by an annular rim 31 adhesively bonded to the underside of the support plate 18 about the entrance to inlet passage 25. Directly below the filter disc 30, the surface of the bottom wall of the casing is provided with parallel ribs 13a that prevent the bottom wall from blocking fluid flow from lower chamber 16 into filter 30 and inlet passage 25 should the bottom wall be flexed upwardly into contact with the filter (FIG. 7).

Figure 5:
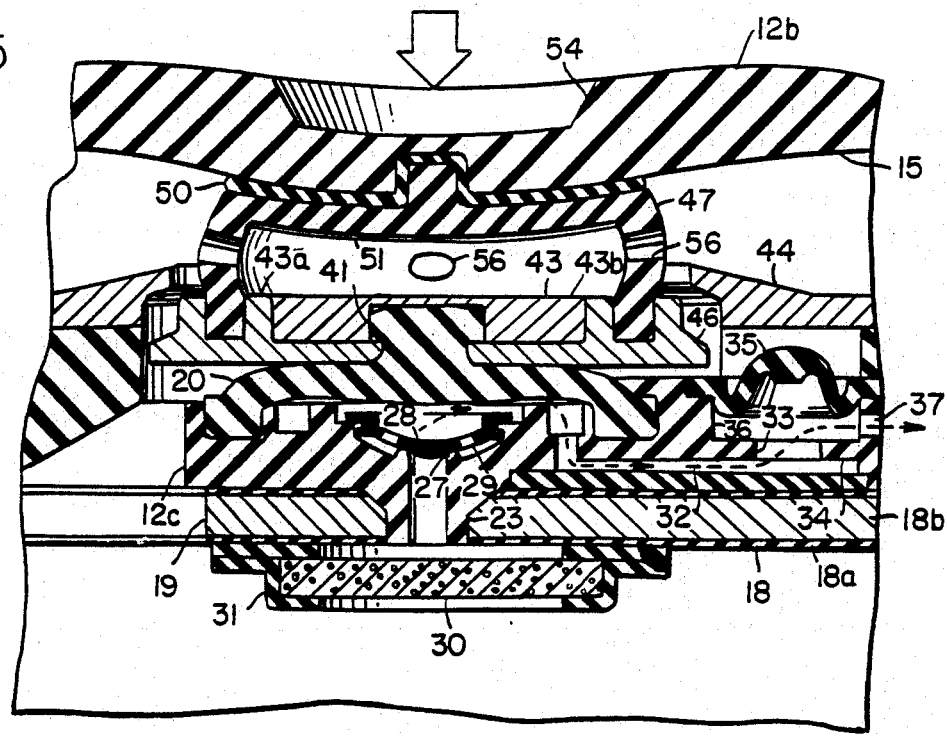
FIG. 5 is a fragmentary sectional view similar to FIG. 4 but illustrating the condition of the device during a pumping step.

A second passage 32 also communicates with the chamber 26 of the pump and leads radially away from the pump through the inner section 12c of the top wall. The second passage 32 is parallel and in close proximity to rigid support plate 18 and communicates at its opposite end with a valve opening 33 defined by an annular flexible lip 34 that is preferably formed integrally with section 12c of the top wall. The lip defines a valve seat and the opening 33 is normally closed by a cup-shaped elastomeric valve member 35 mounted within cylindrical chamber 36. In its normal undeformed state, valve member 35 engages lip 34 to maintain the valve in closed condition; however, as shown in FIG. 5, the valve member is capable of being deformed upwardly into unseated condition to allow fluid flow from secondary passage 32 and opening 33 into chamber 36 and then into outlet passage 37. The outlet passage leads to outlet port 38 which in turn communicates with the lumen of a catheter 39. A tapered ferrule or connector 40 is secured to the casing 11 and supports the catheter at its point of exit from the casing.

All of the elements so far described, except for filter disc 30 and the core 18b of support plate 18, are composed of soft, deformable material. Silicone rubber of the same formulation or different formulations may be used for all of such resilient elements which, as already indicated, are secured together by any suitable adhesive to provide the assembly illustrated in the drawings.

The dome-shaped pump housing 20 has an upstanding stem portion 41 that is anchored to a rigid disc 43 formed of polycarbonate or any other suitable material having sufficient strength, hardness, and rigidity to resist needle penetration. In the illustration given, the disc 43 is formed in two sections 43a and 43b to facilitate assembly, or subassembly, with pump housing 20; however, it is to be understood that if desired the rigid disc 43 may instead be formed in one piece.

Figure 4:
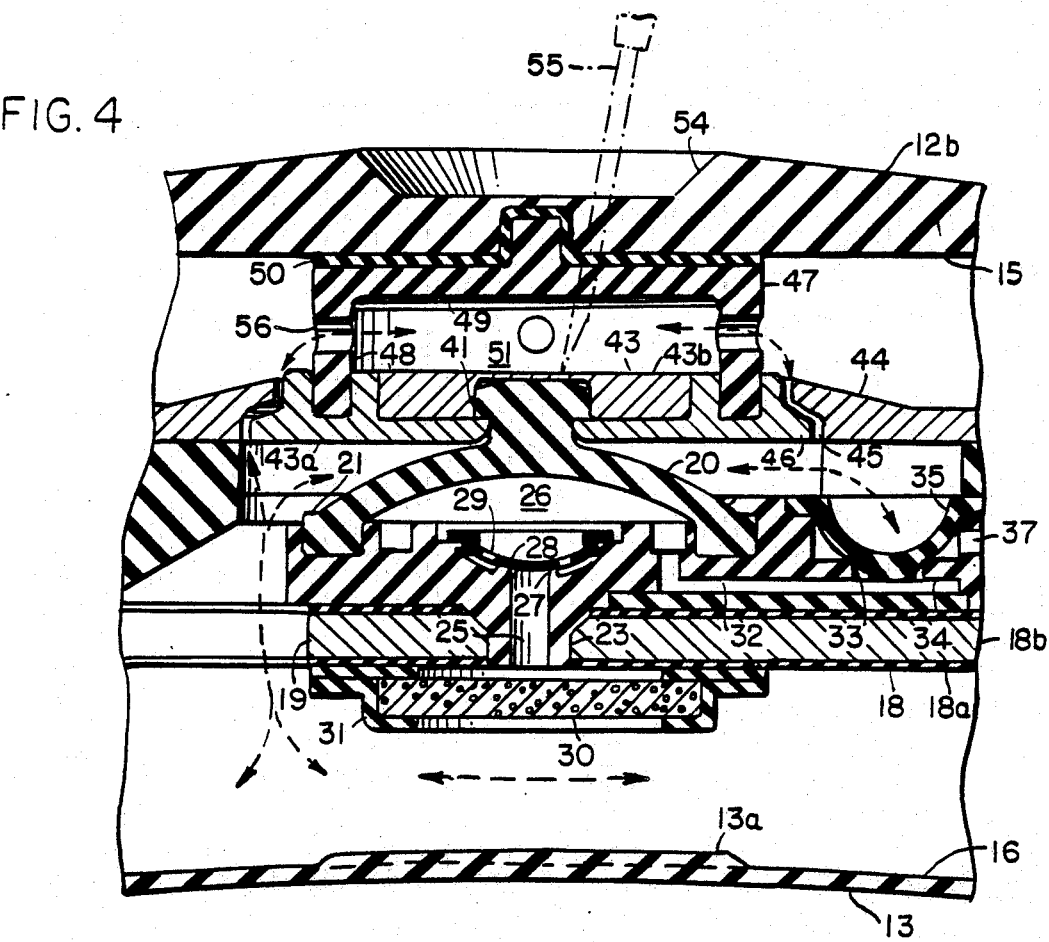
FIG. 4 is a still further enlarged vertical longitudinal sectional view showing the filling port, needle guard, and pump assembly.

The disc 43 is surrounded by an annular plate 44 that is also formed of rigid material, preferably the same material as disc 43. The periphery of the annular plate is locked in place between the central section 12b and the inner section 12c of upper wall 12. As shown in FIGS. 3 and 4, the opposing edges or side surfaces of the disc 43 and annular plate 44 are spaced apart to provide flow passages 45 that maintain the portions of the upper chamber above and below the disc and annular plate in pressure-equalizing flow relation. A rim 46 of the disc 43 projects outwardly and is engagable with the annular plate 44 to limit the extent of upward movement of the disc and, if desired, the rim may be serrated or discontinuous to insure that passages 45 remain open at all times.

Above disc 43 is an inverted cup-shaped septum 47 having an apertured side wall 48 and, when fully assembled, a planar end wall 49. The lower periphery of the side wall 48 is secured within an annular channel provided in rigid disc 43. The septum is formed of an elastomer such as silicone rubber and is secured to the underside of the central section 12b of the casing's top wall 12 by mean of an adhesive attachment layer 50.

Figure 8:
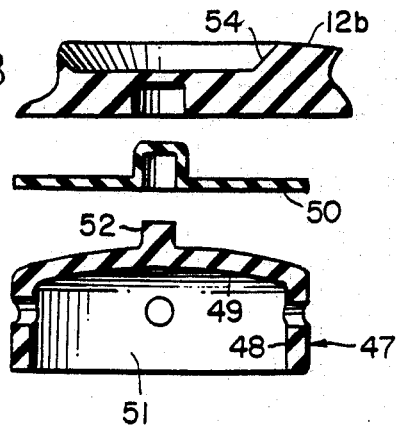
FIG. 8 is an exploded sectional view illustrating the deformable septum and associated parts prior to assembly.
Figure 9:
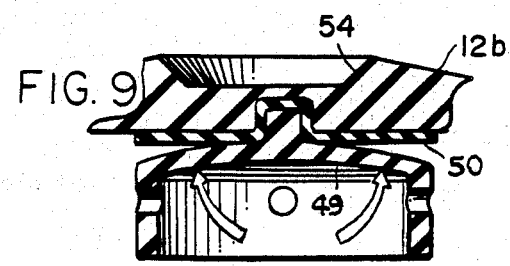
FIG. 9 is a sectional view illustrating the parts of FIG. 8 in partially assembled condition.
Figure 10:
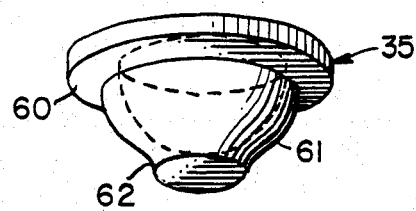
FIG. 10 is an enlarged perspective view illustrating the outlet valve member of the device.

Of particular importance is the fact that end wall 49 of the elastomeric septum is spaced well above disc 43 to define a medicament-receiving chamber 51. Also, while shown in the assembly drawings to be of generally planar configuration (except for locating protuberance 52), the end wall in an untensioned state is dome shaped. As shown in FIG. 8, in the absence of distorting forces the convex end wall 49 curves upwardly and inwardly so that when flattened and adhesively secured to the planar undersurface of the casing's top wall section 12b, the end wall 49 will have its upper surface portion in a compressed state and will be maintained in that compressed state by adhesive layer or pad 50. It has been found that such limited compression of the upper stratum of end wall 49 greatly enhances the self-sealing properties of the septum upon withdrawal of an injection needle.

Ideally, the upper surface of the central section 12b of casing's top wall 12 is provided with an indentation 54 of circular outline. The indentation identifies the target site for both pump actuation and fluid injection and helps a user locate such site by touch even when the fluid delivery device is implanted. When fluid is to be supplied to the reservoir, the needle 55 of a syringe is simply inserted into the casing through the indented zone of the top wall until the tip of the needle engages rigid disc 43 within medicament-receiving chamber 51 (FIG. 4). Discharge of fluid from the syringe flows outwardly through openings 56 in the side wall of septum 47. Since the upper and lower chambers of the reservoir are in communication, such fluid enters the space above the dome-shaped pump housing 20 and above outlet valve member 35, and is free to pass into the lower chamber through opening 19. Upon removal of needle 55, the compressed end wall 49 of the septum 47 then closes and reseals the reservoir.

Figure 6:
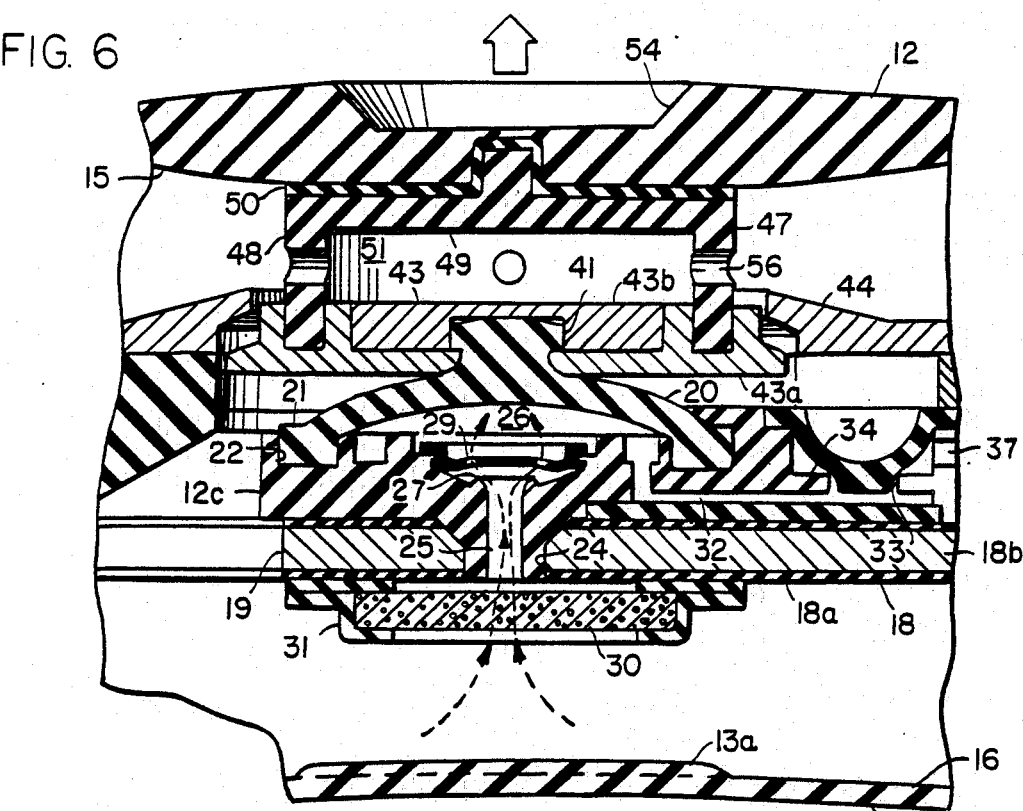
FIG. 6 is a similar fragmentary sectional view showing the parts during a recovery step in which the pump cavity is being refilled.

The same target zone, as defined by indentation 54, is used for finger actuation of the pump mechanism. Depression of the top wall 12 in the area of indentation 54, as depicted in FIG. 5, drives the septum 47 and rigid disc 43 downwardly, deforming pump housing 20 and substantially exhausting pump cavity 26. Fluid in the pump cavity is driven outwardly into second passage 32 with the pressure increase beneath outlet valve 35 causing the outlet valve to flex upwardly into open position. An aliquot of fluid substantially equal to the volume of pump chamber or cavity 26 (when the pump housing is undeformed) is therefore discharged into the outlet passage 37 and through outlet port 38. When finger pressure is removed, the top wall returns to its original position largely because of the recovery forces exerted by the dome-shaped pump housing 20 and the flexible top wall portion 12b. As the pump cavity 26 expands, the pressure differential causes the membrane valve member 28 to lift away from its seat 27, allowing fluid from the lower chamber 16 of the reservoir to enter the pump cavity 26 through the first passage 25 and openings 29 in the membrane (FIG. 6). Once the pump cavity is filled and pressure is equalized, the inlet valve member 28 closes and the parts again assume the relationships depicted in FIGS. 3 and 4.

Since the upper and lower chambers of the reservoir are in open communication at all times, deformations of the resilient casing 11 produced by body movement or other causes do not result in unintentional delivery of medicament to the patient. For example, should patient movement cause compression of the device and subsequent upward flexure of bottom wall 13 from the position shown in FIG. 4, fluid displaced from lower chamber 16 is free to enter the upper chamber of the reservoir, including the area directly above outlet valve member 35. The outlet valve will therefore remain closed despite the deformation of the casing because pressure will be equal on both sides of outlet valve 35. The double-headed arrows in FIG. 4 are intended to indicate the reversibility of movement of fluid throughout the upper and lower chambers of the reservoir that results in pressure equalization.

Referring to FIGS. 10–13, it will be noted that outlet valve member 35 is cup shaped with an upper rim 60 and a semi-spherical body 61. At its lower end, the valve member is provided with a truncated stem or base portion 62 having an outer surface that flares or curves downwardly, thereby deviating from the otherwise semi-cylindrical outer surface contour of the valve member.

Figure 11:
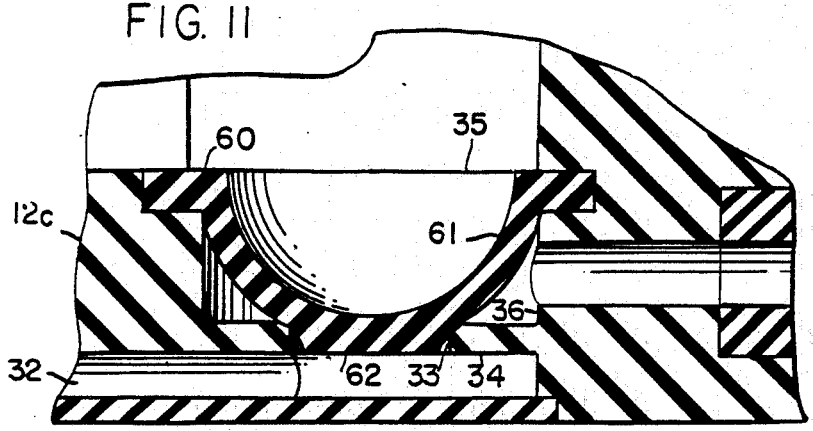
FIG. 11 is an enlarged sectional view showing the relationship of the deformable valve member and deformable valve seat under equalized pressure conditions.
Figure 12:
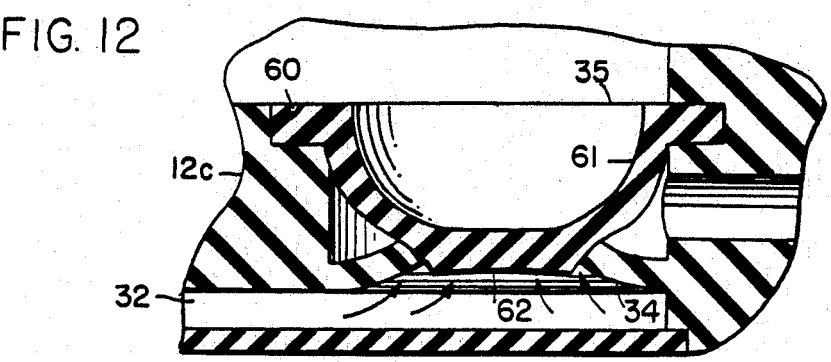
FIG. 12 is a sectional view similar to FIG. 11 but showing deformation of the parts in the early stages of a fluid-delivery operation.
Figure 13:
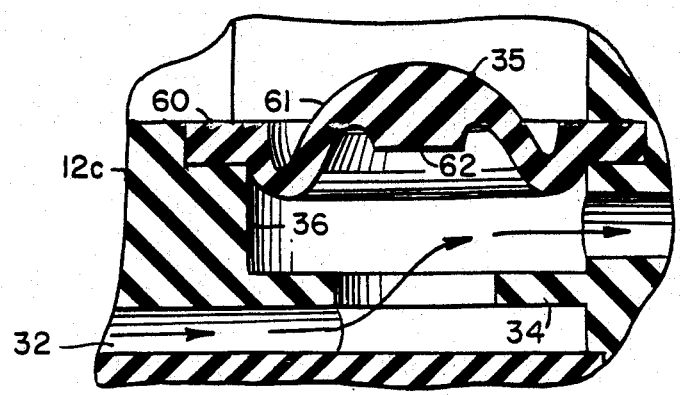
FIG. 13 is a sectional view similar to FIGS. 11 and 12 but showing the parts immediately following breakaway of the valve member from its valve seat.

When the device is at rest, the valve member assumes the condition depicted in FIG. 11. However, at the commencement of a pumping operation when downward force is applied to the target area of the device's top wall 12, fluid displaced from the pumping chamber or cavity 26 causes upward movement of base portion 62 as illustrated in FIG. 12. The annular lip 34 defining the valve seat, being formed of soft, deformable material, also flexes upwardly so that, despite upward displacement of base portion 62, sealing engagement between the lip and the outwardly-curved surface of the base portion persists (FIG. 12). Sealing engagement between the valve member and lip continues as the valve member deforms upwardly until, finally, as a result of increasing pressure, the dome-shaped valve member "collapses" and sudden breakaway from lip 34 occurs. The lip 34 then returns to its planar state and the valve member 35 continues upwardly into its fully opened state (FIG. 13).

Because fluid cannot escape through the outlet valve until finger pressure on the target zone of the casing's top wall has caused the valve member and valve seat to deform beyond the condition depicted in FIG. 12, and because the opening of the valve occurs suddenly when the limits of stability of the dome-shaped valve member are exceeded, the sudden breakaway action provides a tactile feedback signal to the user that may be readily detected through finger contact with the patient's skin overlying the target zone of the device. A user may therefore establish through tactile feedback that a metered dose of medicament has been discharged from the device.

The initial resistance to opening of the outlet valve, until a threshhold limit of deformation is exceeded, also increases security for the patient by preventing or greatly reducing the possibilities of accidental administration of medicament. Substantial force, preferably in the range of 10 to 20 pounds per square inch, must be exerted directly against the target zone, and in the direction of pump housing 20, before breakaway of the outlet valve occurs. While the parts may be fabricated so that such breakaway occurs at any selected threshhold limit, a breakaway pressure of approximately 15 pounds per square inch is preferred.

While in the foregoing, an embodiment of the invention has been disclosed in considerable detail for purposes of illustration, it will be understood by those skilled in the art that many of these details may be varied without departing from the spirit and scope of the invention.

We claim:

1. An implantable patient-activated device for dispensing metered amounts of fluid to such a patient, comprising a casing formed of soft, deformable polymeric material having a top wall and a bottom wall defining a fluid reservoir with an outlet port; pumping means within said casing including a compressible pump housing having a pumping chamber; first passage-providing means defining an inlet passage extending between said reservoir and said chamber; inlet valve means restricting flow through said inlet passage from said chamber to said reservoir; second passage providing means defining an outlet passage extending between said chamber and said outlet port; outlet valve means along said outlet passage for controlling flow therethrough; said outlet valve means including an annular valve seat of elastomeric material providing a valve opening and a cup-shaped valve member formed of elastomeric material having an outer surface normally sealingly engaging said valve seat; said top wall of said casing having a target zone operatively connected to said pump housing and deformable by finger pressure to compass said pump housing; said valve seat and valve member being deformable together, when said target zone is depressed to compass said pump housing and displace fluid from said chamber, until said seat reaches a limit of deformation and said valve member breaks away from said seat to allow fluid to surge through said outlet passage, said breakway and surge providing tactile feedback to signal a user applying finger pressure to said target zone that a metered amount of fluid has been discharged from said device; said body portion of said valve member including a base having a truncated stem portion; said truncated stem portion having an outer surface sealingly engageable with said deformable annular valve seat.

2. The device of claim 1 in which said valve member is cup-shaped and has a rim portion and a generally semispherical body portion; said valve member having an outer surface directed towards said outlet passage and an inner surface directed towards said reservoir.

3. The device of claim 2 in which said rim portion of said valve member is secured to said top wall within said casing.

4. An outlet valve for an implantable patient-activated fluid delivery device, said outlet valve including a deformable annular valve seat of elastomeric material defining a valve opening; and a cup-shaped valve member formed of elastomeric material; said valve member having a generally semi-spherical body portion with an outer surface normally sealingly engaging said annular deformable valve seat; said valve seat and valve member being deformable together, in response to pressure increases applied to said valve seat and to the outer surface of said valve member, until said seat reaches a limit of deformation and said valve member breaks away from said seat to allow a surge of fluid through said valve opening; said body portion including a base in the form of a truncated stem portion; said deformable annular valve seat normally engaging the outer surface of said body portion adjacent said truncated stem portion when said outlet valve is closed.

5. The outlet valve of claim 4 in which said valve seat is defined by an annular lip having generally parallel planar oppositely-facing surfaces when said valve seat is in an undeformed state.

* * * * *